United States Patent [19]
Olexa et al.

[11] 4,427,646
[45] Jan. 24, 1984

[54] USE OF RADIOLABELED PEPTIDE DERIVED FROM CROSSLINKED FIBRIN TO LOCATE THROMBI IN VIVO

[75] Inventors: Stephanie A. Olexa, Hellertown, Pa.; Linda C. Knight, Plainsboro, N.J.; Andrei Z. Budzynski, Glenside, Pa.

[73] Assignee: Research Corporation, New York, N.Y.

[21] Appl. No.: 250,174

[22] Filed: Apr. 2, 1981

[51] Int. Cl.³ ............... A61K 49/00; A61K 43/00; C07G 7/00; C07C 103/52
[52] U.S. Cl. ........................ 424/1.1; 424/9; 424/177; 260/112 B; 260/112.5 R
[58] Field of Search ............ 424/111.5, 4, 519, 177; 260/112.5 R, 112 B

[56] References Cited

U.S. PATENT DOCUMENTS

| | | | |
|---|---|---|---|
| 3,933,996 | 1/1976 | Charlton et al. | 424/1 |
| 4,057,617 | 11/1977 | Abramovici et al. | 424/1 |
| 4,245,051 | 1/1981 | Reich et al. | 424/101 |

OTHER PUBLICATIONS

Budzynski et al., Biochim. Biophys. Acta., 584 (1979) 284–287.
Olexa et al., Biochem., 18 (1979) 991–995.
Olexa et al., Biochem., 20 (1981) 6139–6145.
Olexa et al., Biochim. Biophys. Acta., 576 (1979) 39–50.
Hoots et al., N.E.J. Med., 304 (4-9-1981) 857–861.
Kisiel et al., Biochem., 15 (1976) 4893–4900.
Niemann et al., Biochem. 19 (1980) 1576–1583.
Scully et al., Biochem. Biophys. Res. Comm., 68(1976) 1206–1211.
Mosher, J. Biological Chem., 251 (1976) 1639–1645.

*Primary Examiner*—Christine M. Nucker
*Attorney, Agent, or Firm*—Scully, Scott, Murphy & Presser

[57] ABSTRACT

A method of locating thrombi in vivo comprising the steps of administering a radiolabeled peptide selected from the group consisting of Fragment $E_1$ isolated from cross-linked fibrin, Fragment $E_2$ isolated from cross-linked fibrin, and peptides having an amino acid sequence intermediate between Fragments $E_1$ and $E_2$ derived from crosslinked fibrin by plasmin digestion to a human or animal wherein the peptide is selectively incorporated or bound by forming a pre-formed thrombi and externally detecting the radiation emitted by the radiolabeled peptide. A composition containing the peptide used for locating thrombi is also disclosed.

14 Claims, No Drawings

USE OF RADIOLABELED PEPTIDE DERIVED FROM CROSSLINKED FIBRIN TO LOCATE THROMBI IN VIVO

BACKGROUND OF THE INVENTION

1. Field of the Invention

This invention relates to a method of locating thrombi in humans and animals, and more particularly to the use of a radiolabeled peptide derived from the degradation of crosslinked fibrin by plasmin as an imaging agent for locating thrombi in vivo.

2. Description of the Prior Art

Disorders of the blood clotting system are present in a significant fraction of the human population. The most common such disorder is the formation of thrombi, clots formed in a blood vessel or heart cavity that remain at the point of formation. Thrombi in heart vessels, for example, can restrict blood flow, resulting in myocardial infarction (death of heart muscle), one of the most severe forms of heart attacks.

In addition, parts of a thrombus of the entire thrombus can dislodge from its point of attachment and move through the blood vessels until it reaches a point where the passage is restricted. The resulting sudden blockage of blood flow is known as a thromboembolism. One part of the circulation system particularly subject to emboli formation is in the lungs, the first point at which main arteries divide into smaller arteries and capillaries after the heart has received blood from the venous system. A 1968 study of all hospital deaths showed that pulmonary emboli were present in 50% of patients who died at age 60, and in 64% of those who died at age 70. In the patients with emboli, an embolus was the major cause of death in 43% of the cases. Overall, over 700,000 cases of pulmonary emboli are detected in the United States every year and more than 90% of these emboli can be traced to deep vein thrombosis.

Accordingly, methods which enable thrombi to be detected are of great medical importance so that preventive measures, such as anticoagulant therapy or surgery, can be taken.

In recent years, human fibrinogen labeled with a radioisotope has been used for the detection of thrombi in the deep veins of the leg and in other parts of the body. Fibrinogen can be labeled with iodine-125 (U.S. Pat. No. 3,9833,996) or technetium-99 m (U.S. Pat. No. 4,057,617) and injected via a suitable carrier into a vein where it enters into clot (thrombus) formation. Activation of fibrinogen by the enzyme thrombin causes the release of fibrinopeptides (fibrin monomers), which polymerize to form a fibrin polymer that forms part of a clot or thrombus. When radiolabeled fibrinogen enters into clot formation, the radioactivity becomes localized and the thrombus can be located by external detection of the radiation.

Although the use of radiolabeled fibrinogen has constituted an advance in the location of thrombi, some problems still exist. Fibrinogen is taken up only by relatively fresh or still forming thrombi and hence may not be sufficiently localized in old thrombi (>1 day old) to allow effective external imaging. Accordingly, an imaging agent that would be taken up by both forming thrombi and previously formed thrombi is highly desirable. However, no such agent was known prior to the present invention.

SUMMARY OF THE INVENTION

Accordingly, it is an object of this invention to provide a method of locating both newly formed and previously formed thrombi.

It is another object of this invention to provide a method of locating thrombi by means of a radiolabeled imaging agent that will be selectively taken up by both newly formed and previously formed thrombi which could thereby be located by external measurement of emitted radiation.

These and other objects of the invention, as will hereinafter become more readily apparent, have been achieved by providing a method of locating thrombi in vivo, comprising the steps of administering a radiolabeled peptide selected from the group consisting of Fragment $E_1$ isolated from cross-linked fibrin, Fragment $E_2$ isolated from cross-linked fibrin, and peptides having an amino acid sequence intermediate between Fragments $E_1$ and $E_2$ to a human or animal, wherein said peptide is selectively taken up by thrombi, and externally detecting radiation emitted by said radiolabeled peptide.

DESCRIPTION OF THE PREFERRED EMBODIMENTS

Fragments $E_1$ and $E_2$ are soluble degradation products released from crosslinked fibrin by the action of the enzyme thrombin. These fragments have been previously known and reported, but it was not known that they would be taken up by either fresh or previously formed clots or thrombi.

The relationship between fibrinogen and Fragments $E_1$ and $E_2$ can best be seen when considered in view of clot-forming and clot-breakdown biochemistry.

Human fibrinogen is a soluble plasma protein which is cleaved by the enzyme thrombin and forms insoluble fibrin, the network or matrix of a clot. The fibrin can be covalently crosslinked by Factor XIIIa to form a stabilized clot. Human crosslinked fibrin is degraded by the enzyme plasmin, thereby releasing characteristic degradation products: (DD)E complex, Fragments DD and E, and $\alpha$ polymer remnants. The (DD)E complex is the primary soluble plasmin degradation product released from cross-linked fibrin. This complex is susceptible to further action of plasmin according to the following scheme: crosslinked fibrin→(DD)$E_1$→(DD)$E_2$→D-D+$E_3$. The initial complex contains Fragments DD and $E_1$. Upon further digestion Fragments $E_1$ is cleaved to Fragment $E_2$ without loss of the ability to bind to Fragment DD. Digestion of Fragment $E_2$ to $E_3$ results in dissociation of the complex. Therefore the terminal plasmin digestion products of crosslinked fibrin are Fragments DD and $E_3$. This pattern of digestion is consistant regardless of the plasmin to fibrin ratio; however, the rate of formation of the terminal products differs significantly with the plasmin concentration.

Preparation of various plasmin degradation products has been previously reported by two of the present inventors, Olexa and Budzynski, in *Biochemistry* 18, 991 (1979), and in *J. Biol. Chem.* 254, 4925 (1979) which are hereby incorporated by reference. The basic process reported in these publications for the preparation and isolation of Fragments $E_1$ and $E_2$ begins with the formation of a fibrin clot from fibrinogen enriched with Factor XIII. The clot is hydrolyzed with plasmin and the resulting digest is centrifuged to remove large clot particles. The supernatant contains soluble degradation products, including the desired Fragments $E_1$ and $E_2$. The degradation products are separated according to molecular weight, preferably on an agarose gel bead column, to give the (DD)E complex. Fragments $E_1$ and $E_2$ are obtained from the purified (DD)E complex by incubation in a concentrated salt solution to cause dissociation of DD and $E_1$ or $E_2$ fragments followed by separation according to molecular weight, preferably by means of an agarose gel bead column. A detailed description of the process used is given in the Olexa and Budzynski publications listed above.

Fragments E are the plasmic cleavage product of human crosslinked fibrin which contains the $NH_2$-terminal regions of all six polypeptide chains of fibrinogen. At least three species of Fragment E have been isolated and characterized, i.e. Fragments $E_1$, $E_2$ and $E_3$, of molecular weights 60,000, 55,000 and 50,000. The species are sequential degradation products and microheterogeneity of each species has been noted. Fragments $E_1$ and $E_2$ have the ability to bind to Fragment DD from crosslinked fibrin but do not bind with the DD-E complex, fibrinogen, or any of the plasmic degradation products of fibrinogen or of noncrosslinked fibrin.

In more recent investigations leading to the present invention, the inventors determined that Fragment $E_1$ would incorporate into a forming fibrin clot in an in vitro system. This was the first indication that the $E_1$ fragment would be taken up in a clot. Further investigations indicated that Fragment $E_1$ also became incorporated into preformed clots, formed from normal plasma and aged in serum for 2 hours.

Since Fragment $E_1$ was found to bind to both forming fibrin clots and to preformed, aged fibrin clots but not to bind to soluble fibrinogen or plasma proteins, the inventors recognized that this molecule can act as a tracer to locate in vivo thrombi. Fragment $E_1$ radioactively labeled with $123_I$, $125_I$, $131_I$, $111_{In}$, $^{99m}Tc$ or another appropriate isotopes having gamma radiation suitable for external imaging, can be intravenously injected into a patient suspected of having a thrombus. Periodically areas of the patient's body would be imaged by a gamma camera or scanned with a rectilinear scintillation scanner. An alternative method for surveying the deep veins of the legs employs a hand-held scintillation probe used to take counts at a plurality of points along each leg.

In determining the suitability of Fragment $E_1$ as an in vivo imaging agent, several factors must be taken into consideration. An efficient tracer for the labeling of in vivo thrombi should have the following characteristics: (1) it should be easily labeled with a radioactive isotope to a high specific activity; (2) when injected systemically it should both incorporate specifically and quickly into forming clots and bind to aged clots; (3) unbound material should be quickly removed from the circulation; (4) the material should not bind to fibrinogen or to other soluble plasma proteins; (5) the amount of bound material should decrease as the clot lyses; and (6) the material should be non-antigenic. Fragment $E_1$ meets all of these requirements.

Fragment $E_1$ contains approximately twenty tyrosine residues and about ten histidine residues, and therefore can easily be labeled with radioactive iodine, for example, by the chloramine-T, iodine monochloride, Iodogen (1,3,4,6-tetrachloro-3α,6α-diphenylglycoluril) or lactoperoxidase methods. Radiolabeling with other isotopes can also be easily accomplished, for example, with $^{99m}Tc$ as described in Abramochi et al., U.S. Pat. No. 4,057,617 which is hereby incorporated by reference. Very stable attachment of radioactive metal ions can best be accomplished by using a bifunctional chelating agent, i.e., a molecule containing a metal complexing group which could be attached to the peptide through a covalent linkage. An example of such a bifunctional chelating agent has been described by Krejcarek and Tucker in *Biochem. Biophys. Res. Commun.* 77: 581–585 (1977), which is hereby incorporated by reference. Fragment $E_1$ binds to both forming clots and to aged clots as shown herein. The biological half-life of human Fragment $E_1$ in rabbits is 1.4 hours compared to 49.3 hours for fibrinogen. It is quite probable that human Fragment $E_1$ would have a relatively short half-life in humans as well. Fragment $E_1$ does not bind to fibrinogen or any fibrinogen degradation products, but binds to aligned fibrin monomer molecules in a fibrin strand (Tables 1 and 2). Fragment $E_1$ does not bind to any soluble plasma proteins. Since Fragment $E_1$ can be cleaved to Fragment $E_3$ by plasmin, losing its binding capacity, the Fragment $E_1$ incorporated into a fibrin clot can be cleaved and released into the blood. The loss of radioactive Fragment $E_1$ from the thrombus parallels lysis of the thrombus. Finally, since Fragment $E_1$ may be derived from human fibrinogen, it is not likely to be a potent antigen. In conclusion, Fragment $E_1$ or any part of Fragment $E_1$ which contains the binding sites, would be an efficient tracer for the localization of in vivo thrombi.

Where the product is to be used in the treatment of human beings, the Fragment $E_1$ should preferably be isolated from human crosslinked fibrin, in order to minimize its antigenicity, but for other purposes animal crosslinked fibrin is suitable as a source of Fragment $E_1$.

Fragment $E_1$ may be injected intravenously in any suitable pharmaceutical carrier, either alone or in combination with other therapeutic or diagnostic agents. Suitable carriers are those which dissolve Fragment $E_1$ or hold it in suspension and which are not toxic to the extent of permanently harming the host organism. Preferred are non-toxic aqueous solutions of salts or non-ionic compounds such as sodium chloride or glucose, most preferably at an isotonic concentration. Other drugs may be present provided that they do not interfere with the action of Fragment $E_1$ as an imaging agent. Suitable amounts for combination are 5–95% labeled Fragment $E_1$ and 95–5% other drug or drugs. Particularly suitable are those substances normally injected with thrombus imaging agents, such as heparin.

Fragment $E_1$ may be injected into the blood stream at any convenient point, although injection upstream from and near to the site of the suspected thrombus is prefered.

Suitable amounts for injection depend on the specific radioactivity of the radiolabeled Fragment $E_1$ and can easily be determined by either calculation or simple experimentation. Radiolabeled Fragment $E_1$ should be administered in an amount sufficient to be detected by gamma camera imaging or other external radiation detection means capable of locating the localized radiation present in the thrombus, such as autoradiography. In general, about 10 μCi to 50 mCi of radiation should be injected in order to achieve this effect in humans. The actual amount would depend upon the properties of the radionuclide used (e.g., physical half-life and energies of emitted gamma rays). In general, preferred amounts would be within 50 to 100% of the maximum allowable administered dose (limited by prevalent standards of safety) based on target organ and whole body radiation exposure in experimental subjects.

Analyzing by scintillation scanning or other external detection methods may begin within one hour after injection or may be delayed as many as three days. Better results are generally obtained between 6 and 18 hours after injection.

In terms of amount by weight of radioactive Fragment $E_1$ that is administered, no apparent lower limit exists except for the degree to which Fragment $E_1$ may be labeled with a radioactive isotope. There does not appear to be any upper limit except for those created by solubility if Fragment $E_1$ is isolated from the same species into which it is injected. An upper limit is set for injections of Fragment $E_1$ from a different species by immune reactions, as is well known in the art and determinable by simple experimentation. If the specific radioactivity of the Fragment $E_1$ is known, and the desired radioactivity is known as previously described, the amount of Fragment $E_1$ injected can be easily calculated. For example, if the specific activity is 2 $\mu$Ci/mg, a 5 mg sample would contain 10 $\mu$Ci of radioactivity.

The high thrombus-to-blood ratios obtained with radioiodinated Fragment $E_1$ in fresh and aged thrombi imply that radiolabeled Fragment $E_1$ may have great clinical significance. In addition to detecting thrombi in the veins of the legs, the principal use of radiolabeled fibrin Fragment $E_1$ labeled with a suitable imaging isotope (e.g., $^{123}I$, $^{111}In$, $^{99m}Tc$) would be useful for detection of thrombi or emboli anywhere in the body, for example, in the brain in the case of stroke, in the heart in the case of myocardial infarction, and also for detection of pulmonary emboli, for which there is no specific test at the present time.

In addition, since Fragment $E_2$ also exhibits binding with clots and thrombi, Fragment $E_2$ may be used, as described above for Fragment $E_1$, as a thrombus-imaging agent. Since both $E_1$ and $E_2$ exhibit binding with cross-linked fibrin, it is likely that a peptide having an amino acid sequence intermediate between the sequences present in Fragments $E_1$ and $E_2$ would also exhibit binding and be useful as thrombi imaging agents. Such peptides can be formed by limited proteolytic cleavage of terminal amino acids from the various chains of Fragment $E_1$, and can be labeled with a radioisotope in the same manner as Fragments $E_1$ and $E_2$.

Having generally described the invention, a more complete understanding can be obtained by reference to certain specific examples, which are provided herein for purposes of illustration only and are not intended to be limiting unless otherwise specified.

EXAMPLES

Purification of Fragment $E_1$—$E_2$

Human crosslinked fibrin was digested with plasmin (6 units/g fibrin) for 24 hours at 37° C. Approximately 500 mg of the digest was gel filtered on a Sepharose CL-6B column (2.5×190 cm) in a buffer containing 0.05 M Tris-HCl, 0.028 M sodium citrate 0.1 M sodium chloride, 25 units/ml Trasylol (aprotinin), and 0.02% sodium azide, pH 7.8. Fractions containing the (DD)E complex were diluted with an equal volume of 6 M urea/0.05 M sodium citrate, pH 5.5, and incubated at 37° C. for 1 hour, then rechromatographed on a Sepharose CL-6B column (2.5×190 cm) in the above buffer. This procedure dissociated the (DD)E complex and allowed purification of the Fragment E species.

Fragments $E_1$ and $E_2$ were collected together and separated by chromatography through a 0.6×6 cm DEAE-cellulose column. The elution solvent was a linear gradient of 0 to 0.5 M NaCl in 0.01 M sodium carbonate buffer, pH 8.9. Fractions containing peptide were identified by absorbance at 280 nm. Alternatively, the Fragments E were separated by a preparative isoelectric focusing in a pH gradient of 4 to 6 with a sucrose gradient stabilizer. Pooled fractions were collected and, ampholytes were removed by dialyzing the Fragments E against two 500-fold volumes of 1.0 M sodium chloride, two 500-fold volumes of 0.15 M sodium chloride, and four 500-fold volumes of distilled water, and the fragments were then freeze-dried.

Preparation of Radiolabeled Fragment $E_1$–$E_2$

Purified Fragment $E_1$ or $E_2$ was labeled with radioactive iodine by the iodine monochloride method described by McFarlane in *Biochem. J.*, 62, 135–143 (1956), which is hereby incorporated by reference. The labeled preparation contained 0.9 iodine atoms/Fragment $E_1$ molecule and had a specific radioactivity of 0.5 $\mu$Ci/mg. Fragments $E_2$ and $E_3$ were labeled by the same method. When higher specific activity was desired, as for the animal experiments, the Iodogen method (1,3,4,6-tetrachloro-3$\alpha$,6$\alpha$-diphenylglycoluril) was employed to attach $^{131}I$ or $^{123}I$ to Fragments $E_1$ and $E_2$. Use of Iodogen for iodinating proteins has been described by Fraker and Speck in *Biochem. Biophys. Res. Commun.* 80: 849–857 (1978), which is hereby incorporated by reference. The labeled preparation in this case was trace labeled without carrier and had a specific radioactivity of up to 2 mCi/mg.

Characterization of Fragment $E_1$–$E_3$

The amino acid sequence of Fragments $E_1$, $E_2$ and $E_3$ have been determined. Each Fragment E contains six polypeptide chains, two remnants from each of the A$\alpha$, B$\beta$, and $\gamma$ chains of fibrinogen. The parameters of the Fragment E molecules are outlined in Table 1 based upon the known amino acid sequence of fibrinogen.

Binding Experiments

The ability of Fragments $E_1$ and $E_2$ to associate with or bind to fibrinogen and fragments of fibrinogen or fibrin was tested in a soluble system. Fragment E and the species to be tested were mixed in a 1:1 molar ratio, then analyzed on Tris-glycine polyacrylamide (9%) gels. Fragments $E_1$ and $E_2$ bind only to Fragment DD but not to fibrinogen, Fragments X, Y, D or E (Table 2). This indicates that Fragment E binds only to the aligned D regions of Fragment DD, but not to the monovalent Fragment D domain of fibrinogen or fibrinogen derivatives.

To test this binding on a surface interface, Sepharose-insolubilized fibrinogen, fibrin monomer and a short oligomer of crosslinked fibrin were prepared. Fragments $E_1$ and $E_2$ did not bind to Sepharose-fibrinogen or Sepharose-fibrin monomer, but bound to the cross-linked fibrin oligomer (Table 3). This again indicates that Fragments $E_1$ and $E_2$ do not bind to fibrinogen or fibrin monomer but only to aligned fibrin monomers in a fibrin strand.

TABLE 1

Composition of the polypeptide chains of three species of Fragment E from human crosslinked fibrin based on the amino acid sequence of human fibrinogen

| | | |
|---|---|---|
| $E_1$ | α | 17–78 |
| | α | 17–78 |
| | β | 15–122 |
| | β | 15–122 |
| | γ | 1–62 |
| | γ | 1–62 |
| $E_2$ | α | 17–78 |
| | α | 17–78 |
| | β | 15–121 |
| | β | 54–121 |
| | γ | 1–62 |
| | γ | 1–62 |
| $E_3$ | α | 20–78 |
| | α | 24–78 |
| | β | 54–120 |
| | β | 54–120 |
| | γ | 1–52 |
| | γ | 1–52 |

TABLE 2

DEMONSTRATION OF BINDING BY THE FORMATION OF STABLE COMPLEXES

| Test Material | Source | Treatment | $E_1$ | $E_2$ | $E_3$ | DD | (DD)E |
|---|---|---|---|---|---|---|---|
| DD | Crosslinked fibrin | None | + | + | − | − | − |
| (DD) E | Crosslinked fibrin | None | − | − | − | − | − |
| $E_1$ | Crosslinked fibrin | None | − | − | − | + | − |
| $E_2$ | Crosslinked fibrin | None | − | − | − | − | − |
| $E_3$ | Crosslinked fibrin | None | − | − | − | − | − |
| Fibrinogen | | H | − | − | − | − | − |
| " | | T | − | − | − | + | − |
| X (stage 1) | figrinogen | H | − | − | − | − | − |
| " | " | T | − | − | − | + | − |
| X (STAGE 2) | " | H | − | − | − | − | − |
| " | " | T | − | − | − | + | − |
| Y (stage 2) | " | H | − | − | − | − | − |
| " | " | T | − | − | − | + | − |
| D (stage 2) | " | H | − | − | − | − | − |
| " | " | T | − | − | − | − | − |
| D (stage 3) | " | H | − | − | − | − | − |
| " | " | T | − | − | − | − | − |
| D (stage 2) | Non-crosslinked fibrin | None | − | − | − | − | − |
| D (stage 3) | Non-crosslinked fibrin | None | − | − | − | − | − |
| E (stage 2) | Non-crosslinked fibrin | None | − | − | − | − | − |
| E (stage 3) | Non-crosslinked fibrin | None | − | − | − | − | − |
| E (stage 2) | Fibrinogen | H | − | − | − | − | − |
| " | " | T | − | − | − | − | − |
| E (stage 3) | " | T | − | − | − | − | − |
| " | " | T | − | − | − | − | − |
| NDSK | " | H | − | − | − | − | − |
| " | " | T | − | − | − | + | − |

The binding studies were done either in the presence to hirudin (H) at 10 ATU/mg protein or thrombin (T) at 20 NIH units/mg or in the absence of any of these agents.
NDSK = $NH_2$-terminal disulfide knot
+ = binding
− = absence of binding

TABLE 3

BINDING OF FIBRINOGEN AND FIBRIN DERIVATIVES TO INSOLUBILIZED FIBRINOGEN, FIBRIN MONOMER AND CROSSLINKED FIBRIN

| | Amount of Protein Bound to Insolubilized | | | | | |
|---|---|---|---|---|---|---|
| | Fibrinogen | | Fibrin Monomer | | Crosslinked Fibrin | |
| Derivative | mg | nmoles | mg | nmoles | mg | nmoles |
| Fragment $E_1$ | 0 | 0 | 0 | 0 | 1.2 | 20.0 |
| Fragment $E_2$ | 0 | 0 | 0 | 0 | 0.9 | 16.1 |
| Fragment $E_3$ | 0 | 0 | 0 | 0 | 0 | 0 |
| NDSK | 0 | 0 | 0.05 | 1.0 | 0.04 | 0.81 |
| NDSK (thrombin treated) | 0.4 | 6.66 | 0.825 | 13.8 | 0.716 | 11.9 |

Incorporation of Fragment $E_1$ Into Fibrin Clots

Fragment $E_1$ was tested for the ability to incorporate into a forming fibrin clot in an in vitro system. Fragments $E_1$ and $E_3$, radioactively labeled with 125-Iodine, were added to normal human plasma. Clotting was initiated by the addition of thrombin, then the clot was wound out onto a glass rod. The radioactivity in the clot and in the serum was measured. Each concentration of Fragment E was tested in triplicate. The mean value is shown in Table 4. A significant proportion of the Fragment $E_1$ became incorporated into the fibrin clot while the Fragment $E_3$ remained in the serum. Therefore, Fragment $E_1$ can bind to a forming fibrin clot.

Binding of Fragment $E_1$ to Preformed Plasma Clots

Plasma clots were formed from 0.5 ml of normal human plasma, suspended on a wire coil and aged in the serum for 2 hours. The 125-Iodine labeled Fragments $E_1$ or $E_3$ were added to the serum and incubation continued for 1 hour. The clots were washed five times in 0.5 ml of 0.15 M sodium chloride. The radioactivity in the serum, washes and in the clot was measured. The Fragment $E_1$ bound to the clot but Fragment $E_3$ did not bind (Table 5). The amount of Fragment $E_1$ bound to a preformed or aged clot was lower than the amount incorporated into a forming clot and proportional to the surface area of the clot.

TABLE 4

INCORPORATION OF FRAGMENTS $E_1$ AND $E_3$ INTO FORMING FIBRIN CLOTS

| 125-I Fragment E | Concentration $E^a$ (M) | Concentration Fibrinogen$^a$ (M) | % Incorporated$^b$ |
|---|---|---|---|
| $E_1$ | $7.2 \times 10^{-9}$ | $4.4 \times 10^{-6}$ | 72.1% |
| | $3.6 \times 10^{-9}$ | $4.4 \times 10^{-6}$ | 44.3% |
| | $1.8 \times 10^{-9}$ | $4.4 \times 10^{-6}$ | 35.4% |
| | $0.9 \times 10^{-9}$ | $4.4 \times 10^{-6}$ | 30.4% |
| | $0.45 \times 10^{-9}$ | $4.4 \times 10^{-6}$ | 32.8% |
| | $0.275 \times 10^{-9}$ | $4.4 \times 10^{-6}$ | 30.4% |
| $E_3$ | $7.2 \times 10^{-9}$ | $4.4 \times 10^{-6}$ | 1.6% |
| | $3.6 \times 10^{-9}$ | $4.4 \times 10^{-6}$ | 1.4% |
| | $1.8 \times 10^{-9}$ | $4.4 \times 10^{-6}$ | 1.2% |
| | $0.9 \times 10^{-9}$ | $4.4 \times 10^{-6}$ | 1.5% |
| | $0.45 \times 10^{-9}$ | $4.4 \times 10^{-6}$ | 1.1% |
| | $0.275 \times 10^{-9}$ | $4.4 \times 10^{-6}$ | 1.2% |

$^a$The initial concentration for fibrinogen and Fragment E are presented
$^b$The percent of total radioactivity that remains with the compressed, washed clot, the mean of triplicate samples.

TABLE 5
BINDING OF FRAGMENTS E₁ AND E₃ TO A PREFORMED CLOT

| 125-I Fragment E | Concentration E[a] (M) | Concentration Fibrinogen[a] (M) | % Incorporated[b] |
|---|---|---|---|
| E₁ | 7.2 × 10⁻⁹ | 4.4 × 10⁻⁶ | 14.1% |
|   | 3.6 × 10⁻⁹ | 4.4 × 10⁻⁶ | 9.8% |
|   | 1.8 × 10⁻⁹ | 4.4 × 10⁻⁶ | 8.4% |
|   | 0.9 × 10⁻⁹ | 4.4 × 10⁻⁶ | 8.3% |
|   | 0.45 × 10⁻⁹ | 4.4 × 10⁻⁶ | 7.6% |
|   | 0.275 × 10⁻⁹ | 4.4 × 10⁻⁶ | 7.0% |
| E₃ | 7.2 × 10⁻⁹ | 4.4 × 10⁻⁶ | 0.13% |
|   | 3.6 × 10⁻⁹ | 4.4 × 10⁻⁶ | 0.11% |
|   | 1.8 × 10⁻⁹ | 4.4 × 10⁻⁶ | 0.19% |
|   | 0.9 × 10⁻⁹ | 4.4 × 10⁻⁶ | 0.21% |
|   | 0.45 × 10⁻⁹ | 4.4 × 10⁻⁶ | 0.21% |
|   | 0.275 × 10⁻⁹ | 4.4 × 10⁻⁶ | 0.13% |

[a]The initial concentrations for fibrinogen and Fragment E are presented
[b]The percent of total radioactivity that remains with the compressed, washed clot, the mean of triplicate samples.

Incorporation of Radioiodinated Fragment E₁ Into Thrombi In Vivo

To test the potential of systemically injected radiolabeled Fragment E₁ for thrombus localization in humans with thrombosis, an in vivo model of thrombosis in animals was used. Because a thrombus is structurally heterogeneous (unlike clots), and because blood circulation and natural catabolic mechanisms can affect the uptake of tracers in vivo, there experiments were important in predicting the success of radiolabeled Fragment E₁ as a radiopharmaceutical for clinical thrombus localization.

Pigs were selected as the experimental animal model, as they are known to be quite similar to humans with respect to cardiovascular diseases, as described in Pond et al., "The Pig as a Model in Biomedical Research" in *The Biology of the Pig*, Comstock Pub. Assoc.) pp. 31–35, 1978. Thrombi were induced in the jugular veins of young pigs weighing 25–50 lb by a locally applied electric current. The method is known to produce thrombi which are morphologically similar to naturally occurring thrombi. After induction, the thrombi were allowed to age for up to 5 days prior to injection of radioiodinated Fragment E₁ into the pig. This permitted the study of tracer uptake in thrombi of various ages, ranging from very fresh thrombi in which fibrin deposition is active, to aged thrombi in which fibrin deposition is likely to be very low. In most cases, ¹²⁵I-labeled fibrinogen was injected simultaneously with the ¹³¹I- or ¹²³I-labeled Fragment E₁, in order to directly compare the thrombus uptake of the two tracers. Radioiodinated fibrinogen is a tracer currently used for clinical detection of forming Deep Vein Thrombosis, and its thrombus uptake behavior has been well studied. Twenty-four hours after injection of the radiotracers, the thrombi were surgically removed and blood samples were drawn. The samples were weighed and counted.

The results of these experiments are listed in Table 6, for all ages of thrombi tested. A high target-to-background ratio is desirable in order to permit external imaging of a thrombus by a gamma scintillation camera. Because the main source of background radiation in thrombus imaging is likely to be due to blood pool radioactivity, the extent of localization in our experimental thrombi is expressed as a thrombus-to-blood ratio, which is defined as:

$$\frac{\text{Thrombus radioactivity per gram}}{\text{Blood radioactivity per gram}}$$

A thrombus:blood ratio of 4 is believed to be sufficient for imaging a thrombus in the veins of the legs, and a ratio of 6 to 8 may be necessary for imaging of thrombi in the chest. The results in Table 6 indicate that radioiodinated fibrinogen is appreciably localized only in very fresh thrombi (less than 20 hours old). Radioiodinated Fragment E₁, however, is localized to an impressive extent in thrombi of all ages tested (0–5 days). Because Fragment E₁ is thought to bind to the surface of a thrombus, the variation in uptake seen here may be due to differences in available thrombus surface area from animal to animal.

TABLE 6
THROMBUS UPTAKE IN PIGS OF RADIOIODINATED HUMAN FRAGMENT E₁

| Thrombus Age (hr) | FRAGMENT E₁ Thrombus:Blood Ratio | FIBRINOGEN Thrombus:Blood Ratio |
|---|---|---|
| 1.25 | 10.4 | 41 |
| 4.4 | 10.0 | 18.8 |
| 5.6 | 108 | 16.9 |
| 20.5 | 9.5 | 2.8 |
| 23 | 17.5 | 3.9 |
|   | 8.5 |   |
| 24 | 40.5 |   |
|   | 9 | 0.5 |
|   | 15 | 1.2 |
| 26 | 14.4 | 1.3 |
| 28.5 | 14 | 2.3 |
| 33 | 8.1 | 1.8 |
| 47 | 57 | 2.4 |
| 48 | 45 | 1.2 |
| 72 | 107 | 2.6 |
| 95 | 42 |   |
| 120 | 18 |   |

Having now fully described the invention, it will be evident to one of ordinary skill in the art that many changes and modifications can be made thereto without departing from the spirit or scope of the invention as set forth herein.

What is claimed as new and intended to be covered by Letters Patent is:

1. A method of locating a thrombus, comprising the steps of:
   administering a radiolabeled peptide selected from the group consisting of Fragment E₁ isolated from cross-linked fibrin, Fragment E₂ isolated from cross-linked fibrin, and peptides having an amino acid sequence intermediate between Fragments E₁ and E₂ to a human or animal, and
   externally detecting radiation emitted by said radiolabeled peptide.

2. The method of claim 1, wherein said peptide is labeled with a radioactive isotope of iodine, technetium, or indium.

3. The method of claim 2, wherein said peptide is radiolabeled with ¹²⁵I or ⁹⁹ᵐTc.

4. The method of claim 1, wherein said administering is by intravenous injection.

5. The method of claim 4, wherein said administering is in the presence of a pharmaceutically acceptable carrier.

6. The method of claim 1, wherein said detecting is by scintillation scanning, gamma camera imaging or hand-held probe.

7. The method of claim 1, wherein radiolabeled Fragment $E_1$ is administered to a human.

8. The method of claim 1, wherein said Fragment $E_1$ has an amino acid sequence identical to that of human fibrinogen amino acids $\alpha$, 17–78; $\alpha$, 17–78; $\beta$, 15–122; $\beta$, 15–122; $\gamma$, 1–62; and $\gamma$, 1–62 and wherein said Fragment $E_2$ has an amino acid sequence identical to that of human fibrinogen amino acids $\alpha$, 17–78; $\alpha$, 17–78; $\beta$, 15–121; $\beta$, 54–121; $\gamma$, 1–62; and $\gamma$, 1–62.

9. A composition used for locating a thrombus, comprising:
radiolabeled peptide selected from the group consisting of Fragment $E_1$ isolated from cross-linked fibrin, Fragment $E_2$ isolated from cross-linked fibrin, and peptides having an amino acid sequence intermediate between Fragments $E_1$ and $E_2$ in an amount sufficient to enable external detection and location of said thrombus, and
a pharmaceutically acceptable carrier suitable for intravenous injection.

10. The composition of claim 9, wherein said peptide is labeled with a radioactive isotope of iodine, technetium, or indium.

11. The composition of claim 9, wherein said peptide is labeled with $^{111}$In, $^{99m}$Tc, $^{125}$I, $^{131}$I or $^{123}$I.

12. The composition of claim 9, wherein said carrier is a non-toxic isotonic aqueous solution of a salt or a non-ionic compound.

13. The composition of claim 12, wherein said carrier is a non-toxic isotonic aqueous solution of NaCl or glucose.

14. The composition of claim 9 wherein said composition further comprises heparin.

* * * * *